(12) United States Patent
Wang et al.

(10) Patent No.: US 11,398,012 B2
(45) Date of Patent: Jul. 26, 2022

(54) MEDICAL IMAGING METHOD AND SYSTEM

(71) Applicant: GE Precision Healthcare LLC, Wauwatosa, WI (US)

(72) Inventors: Dejun Wang, Beijing (CN); Yaan Ge, Beijing (CN); Yan Sun, Beijing (CN); Buer Qi, Beijing (CN); Huanzhong Li, Beijing (CN)

(73) Assignee: GE Precision Healthcare LLC, Wauwatosa, WI (US)

( * ) Notice: Subject to any disclaimer, the term of this patent is extended or adjusted under 35 U.S.C. 154(b) by 161 days.

(21) Appl. No.: 16/902,330

(22) Filed: Jun. 16, 2020

(65) Prior Publication Data

US 2020/0394758 A1 Dec. 17, 2020

(30) Foreign Application Priority Data

Jun. 17, 2019 (CN) .................. 201910519964.X (51) Int. Cl.
*G06T 5/00* (2006.01)
*G06T 5/50* (2006.01)

(52) U.S. Cl.
CPC ............... *G06T 5/001* (2013.01); *G06T 5/50* (2013.01); *G06T 2207/10116* (2013.01); *G06T 2207/20081* (2013.01); *G06T 2207/20084* (2013.01)

(58) Field of Classification Search
CPC . G06T 2207/20084; G06T 2207/20081; G06T 5/002; G06T 11/008; G06T 2207/30004; G06T 2207/10081; G06T 2207/10116; G06K 9/40
See application file for complete search history.

(56) References Cited

U.S. PATENT DOCUMENTS

| 6,084,981 | A | 7/2000 | Horiba | |
| 6,819,790 | B2 * | 11/2004 | Suzuki | ................ G06T 7/0012 |
| | | | | 382/130 |
| 8,923,580 | B2 | 12/2014 | Dekel | |
| 10,290,084 | B1 * | 5/2019 | Podilchuk | ................ G06T 7/13 |
| 10,635,943 | B1 * | 4/2020 | Lebel | ...................... G06T 5/50 |
| 2016/0104057 | A1 | 4/2016 | Shen | |
| 2017/0185871 | A1 | 6/2017 | Zhang | |
| 2018/0349759 | A1 * | 12/2018 | Isogawa | .............. G06N 3/0454 |
| 2019/0042894 | A1 * | 2/2019 | Anderson | ............ G06K 9/6293 |
| 2019/0104940 | A1 | 4/2019 | Zhou | |
| 2020/0128106 | A1 * | 4/2020 | McCormack | .......... G06N 20/20 |

(Continued)

FOREIGN PATENT DOCUMENTS

JP 2018089301 A 6/2018

OTHER PUBLICATIONS

F. Altaf, S. M. S. Islam, N. Akhtar and N. K. Janjua, "Going Deep in Medical Image Analysis: Concepts, Methods, Challenges, and Future Directions," in IEEE Access, vol. 7, pp. 99540-99572, 2019, doi: 10.1109/ACCESS.2019.2929365.*

(Continued)

*Primary Examiner* — Li Liu (57) ABSTRACT

The present application provides a medical imaging method and system and a non-transitory computer-readable storage medium. The medical imaging method comprises obtaining an original image acquired by an X-ray imaging system, and post-processing the original image based on a trained network to obtain an optimized image after processing.

11 Claims, 6 Drawing Sheets

(56) References Cited

U.S. PATENT DOCUMENTS

2020/0202502 A1* 6/2020 Tsymbalenko ............ G06T 5/50
2020/0234080 A1* 7/2020 Ciller Ruiz ........... G06T 11/008
2020/0286214 A1* 9/2020 Kaneko ................. G06T 7/0012

OTHER PUBLICATIONS

European application No. 20180117.2 filed Jun. 20, 2020—European extended Search Report dated Oct. 13, 2020; 3 pages.
JP application 2020-103470 filed Jun. 16, 2020—Office Action dated Sep. 21, 2021, Machine Translation Sep. 22, 2021; 4 pages.
JP2018089301—English Abstract: Espacenet—search results Nov. 17, 2021.
Image-To-Image Translation With Conditional Adversarial Networks; Isola et al.; https://arxiv.org/pdf/1611.07004.pdf; 2018; 17 pages.

* cited by examiner

MEDICAL IMAGING METHOD AND SYSTEM

CROSS-REFERENCE TO RELATED APPLICATIONS

This application claims the benefit of Chinese Patent Application No. 201910519964.X filed on Jun. 17, 2019, the disclosure of which is herein incorporated by reference in its entirety.

TECHNICAL FIELD

The present invention relates to a medical imaging technology, and more specifically, to a medical imaging method and system and a non-transitory computer-readable storage medium.

BACKGROUND

In an X-ray imaging system, radiation from a source irradiates upon a subject, where the subject is usually a patient in medical diagnosis applications. Part of the radiation passes through the patient and impacts a detector, where the detector is divided into a matrix of discrete elements (for example, pixels). Detector elements are read to generate output signals based on the quantity or intensity of radiation impacting each pixel region. The signals may then be processed to generate a medical image that can be displayed for inspection, where the medical image may be displayed in a display device of the X-ray imaging system.

The image quality of the medical image obtained based on the signals acquired by the detector is usually undesirable, and post-processing (such as noise reduction, detail enhancement, and contrast adjustment) needs to be performed on the medical image to improve image quality. In this process, however, image processing parameters are mutually dependent, and the adjustment of a specific post-processing parameter may affect the post-processing effect of other parameters. For example, the contrast of the medical image is adjusted based on a contrast parameter, but the adjustment of this parameter may affect some details of the medical image (for example, obscure some key details); accordingly, processing of background noise of the medical image may affect the details (or contrast or other aspects) of the medical image. As a result, obtaining an ideal optimized image by adjusting the corresponding parameter in each post-processing process is difficult and requires repeated attempts.

SUMMARY

The present invention provides a medical imaging method and system and a non-transitory computer-readable storage medium. In the imaging method, a network is constructed and trained based on a deep learning technique, and an original image acquired by an X-ray imaging system is inputted to the network, so that an optimized image after post-processing can be obtained (outputted), where the optimized image has good performance in aspects such as contrast, detail enhancement, and noise reduction.

An exemplary embodiment of the present invention provides a medical imaging method, the method comprising obtaining an original image acquired by an X-ray imaging system; and post-processing the original image based on a trained network to obtain an optimized image after processing.

An exemplary embodiment of the present invention further provides a non-transitory computer-readable storage medium for storing a computer program, wherein when executed by a computer, the computer program causes the computer to execute instructions for the medical imaging method described above.

An exemplary embodiment of the present invention further provides a medical imaging system, the system comprising a control module and a post-processing module. The control module is configured to obtain an original image acquired by an X-ray imaging system, and the post-processing module is configured to post-process the original image based on a trained network to obtain an optimized image after processing.

Other features and aspects will become clear through the following detailed description, accompanying drawings, and claims.

BRIEF DESCRIPTION OF THE DRAWINGS

The present invention may be better understood by describing exemplary embodiments of the present invention with reference to accompanying drawings, in which.

DETAILED DESCRIPTION

Specific implementation manners of the present invention will be described in the following. It should be noted that during the specific description of the implementation manners, it is impossible to describe all features of the actual implementation manners in detail in this description for the sake of brief description. It should be understood that in the actual implementation of any of the implementation manners, as in the process of any engineering project or design project, a variety of specific decisions are often made in order to achieve the developer's specific objectives and meet system-related or business-related restrictions, which will vary from one implementation manner to another. Moreover, it can also be understood that although the efforts made in such development process may be complex and lengthy, for those of ordinary skill in the art related to content disclosed in the present invention, some changes in design, manufacturing, production or the like based on the technical content disclosed in the present disclosure are only conventional technical means, and should not be construed as that the content of the present disclosure is insufficient.

Unless otherwise defined, the technical or scientific terms used in the claims and the description are as they are usually understood by those of ordinary skill in the art to which the present invention pertains. The words "first," "second" and similar words used in the description and claims of the patent application of the present invention do not denote any order, quantity, or importance, but are merely intended to distinguish between different constituents. "One," "a" and similar words are not meant to be limiting, but rather denote the presence of at least one. The word "include," "comprise" or a similar word is intended to mean that an element or article that appears before "include" or "comprise" encompasses an element or article and equivalent elements that are listed after "include" or "comprise," and does not exclude other elements or articles. The word "connect," "connected" or a similar word is not limited to a physical or mechanical connection, and is not limited to a direct or indirect connection.

In an X-ray imaging system, due to mutual influence between various adjusting parameters in the post-processing process, a specific parameter may affect other post-processing processes. The medical imaging method and system in some embodiments of the present invention can post-process an original image obtained by the X-ray imaging system based on a deep learning technique and directly obtain an optimized image after post-processing. Based on this, the difficulty of parameter adjustment would be lowered and the adjustment time in the post-processing process would be reduced. The image quality of the optimized image obtained after post-processing would also be improved. In addition, different learning networks are trained according to preferences of different users (for example, doctors), and a network is selected according to an instruction of a user, so that optimized images of different styles (namely, preferences of different users) can be obtained. It should be noted that from the perspective of those of ordinary skill in the art or related art, such description should not be construed as limiting the present invention only to a digital X-ray imaging system. In fact, the medical imaging method and system described here may be reasonably applied to other imaging fields in medical fields or non-medical fields, such as CT systems, MR systems, PET systems, SPECT systems, or any combination thereof.

Figure 1:
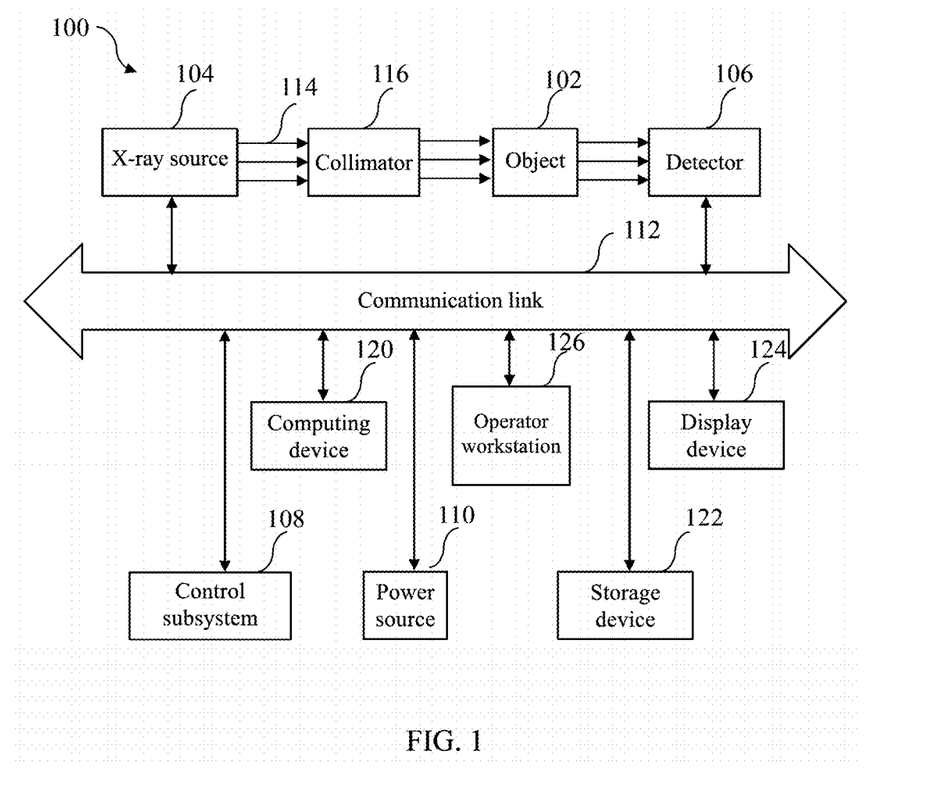
FIG. 1 is a schematic diagram of an X-ray imaging system according to some embodiments of the present invention.

FIG. 1 shows an X-ray imaging system 100 according to some embodiments of the present invention. As shown in FIG. 1, the X-ray imaging system 100 includes an X-ray source 104, a detector 106, and a control subsystem 108. In some embodiments, the X-ray imaging system 100 may be a fixed X-ray imaging system disposed in a fixed X-ray imaging chamber, or may be a mobile X-ray imaging system.

The X-ray source 104 may project X-rays 114 to an expected region of interest (ROI) in a detected object 102. Specifically, the X-ray source 104 may be positioned adjacent to a collimator 116, and the collimator 116 is configured to aim the X-rays 114 at the expected ROI in the detected object 102. At least some of the X-rays 114 may be attenuated through the detected object 102 and may be incident upon the detector 106.

The detector 106 includes a detector panel array which includes a pixel array of a photosensitive photodiode and a switching thin-film field effect transistor (FET) and converts photons into electrical signals. A scintillator material deposited on the pixel array of the photodiode and the FET converts incident X-ray radiation photons received on the surface of the scintillator material into photons with low energy. As mentioned above, the pixel array of the photodiode and the FET converts photons into electrical signals. Alternatively, the detector panel array may directly convert X-ray photons into electrical signals. These electrical signals are provided by a detector panel array interface (which provides digital signals) to a computing device 120 to be converted into image data and to reconstruct a medical image of the detected object 102. In some embodiments, the detector 106 may be configured to convert incident X-rays 114 into electrical signals using light conversion, direct conversion, and/or any other suitable detection technique. In some embodiments, the detector 106 includes a wireless communication interface and a wired communication interface for wireless communication with a communication link 112, which are configured to perform wireless and/or wired communication with the control subsystem 108. The wireless communication interface may use any suitable wireless communication protocol such as an ultra-wideband (UWB) communication standard, a Bluetooth communication standard, or any IEEE 802.11 communication standard.

The detector 106 may further be configured to transfer unprocessed or partially processed image data to a workstation or a portable detector control device via a wired or wireless connection or transfer a processed X-ray image to a printer to generate a copy of the image. The portable detector control device may include a personal digital assistant (PDA), a palmtop computer, a laptop computer, a smart phone, a tablet computer such as an iPad™, or any suitable general- or special-purpose portable interface device. The portable detector control device is configured to be held by a user and perform wireless communication with the detector 106. Note that the detector and the portable detector control device may use any suitable wireless communication protocol, such as an IEEE 802.15.4 protocol, a UWB communication standard, a Bluetooth communication standard, or any IEEE 802.11 communication standard. Alternatively, the portable detector control device may be configured to be connected or detachably connected to the detector 106 for communication via a wired connection.

The control subsystem 108 includes a source controller (not shown in the figure) and a detector controller (not shown in the figure). The source controller is configured to instruct the X-ray source 104 to emit X-rays 114 for image exposure. The detector controller is configured to coordinate control of various detector functions, such as executing various signal processing and filtering functions. Specifically, examples include initial adjustment of a dynamic range, interleaving of digital image data, and so on. In some embodiments, the control subsystem 108 may provide power and timing signals for controlling the operation of the X-ray radiation source 104 and the detector 106. Exactly speaking, the control subsystem 108 may provide power and timing signals to the X-ray radiation source 104 and/or the detector 106 by using a power source 110 and one or a plurality of wired and/or wireless communication links 112, where the communication links 112 may correspond to a backplane bus, a local area network, a wide area network and/or the Internet. In some embodiments, the power source 110 includes one or a plurality of batteries. In addition, although FIG. 1 shows that the power source 110 is connected to the X-ray source 104 through the communication link, those skilled in the art should understand that the power source 110 may also be directly coupled to the X-ray source 104.

The control subsystem 108 may be configured and/or arranged for use in different manners. For example, in some implementations, a single control subsystem 108 may be used. In other implementations, a plurality of control subsystems 108 are configured to work together (for example, configured based on distributed processing) or separately, where each control subsystem 108 is configured to handle specific aspects and/or functions, and/or to process data used to generate a model used only for a specific medical imaging system. In some implementations, the control subsystem 108 may be local (for example, in the same place as one or a plurality of X-ray imaging systems 100, such as in the same facility and/or the same local network). In other implementations, the control subsystem 108 may be remote and thus can only be accessed via a remote connection (for example, via the Internet or other available remote access technologies). In a specific implementation, the control subsystem 108 may be configured in a cloud-like manner, and may be accessed and/or used in a manner substantially similar to that of accessing and using other cloud-based systems.

In some embodiments, the system 100 further includes a computing device 120. The computing device 120 may be configured to use digitized signals to reconstruct one or a plurality of required images and/or determine useful diagnostic information corresponding to the detected object 102, where the computing device 120 may include one or a plurality of dedicated processors, graphics processing units, digital signal processors, microcomputers, microcontrollers, application-specific integrated circuits (ASICs), field programmable gate array (FPGA) or other suitable processing devices.

In some embodiments, the system 100 further includes a storage device 122, where the computing device 122 may store the digitized signals in the storage device 122. For example, the storage device 122 may include a hard disk drive, a floppy disk drive, a CD-read/write (CD-R/W) drive, a digital versatile disc (DVD) drive, a flash drive, and/or a solid-state storage device. The storage device is configured to store a program executable by a computer, and when the computer executes the program, a plurality of components of the X-ray imaging system are enabled to implement operations corresponding to the aforementioned imaging sequence. When the computer executes the program, a medical imaging method may also be performed to post-process the original image to obtain an optimized image after post-processing.

Although FIG. 1 illustrates the storage device 122, the computing device 120, and the control subsystem 108 as separate devices, in some embodiments, one or a plurality of them may be combined into a single device to effectively utilize the floor space and/or meet expected imaging requirements.

In one embodiment, the system 100 further includes a display device 124. The display device 124 may be configured to display a reconstructed image and/or diagnostic information, or the like. For example, the display device 124 may display the original image and/or optimized image described above, and a graphical display interface thereof will be further described in conjunction with FIG. 3.

In one embodiment, the system 100 further includes an operator workstation 126. The operator workstation 126 allows the user to receive and evaluate the reconstructed image, and input a control instruction (an operating signal or a control signal). The operator workstation 126 may include a user interface (or a user input apparatus), such as a keyboard, a mouse, a voice activation controller, or any other suitable input apparatus in the form of an operator interface. An operator may input an operating signal/control signal, for example, one or a plurality of scanning parameters, to the control subsystem 108 through the user interface and/or request required diagnostic information and/or image to evaluate the internal structure and/or function of the detected object 102.

Figure 2:
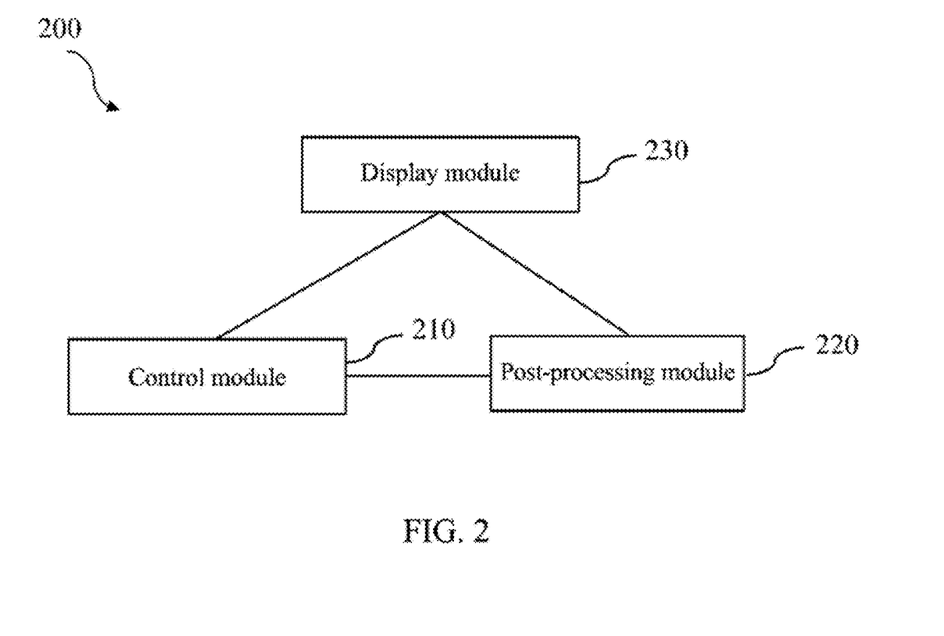
FIG. 2 is a schematic diagram of a medical imaging system according to some embodiments of the present invention.
Figure 3:
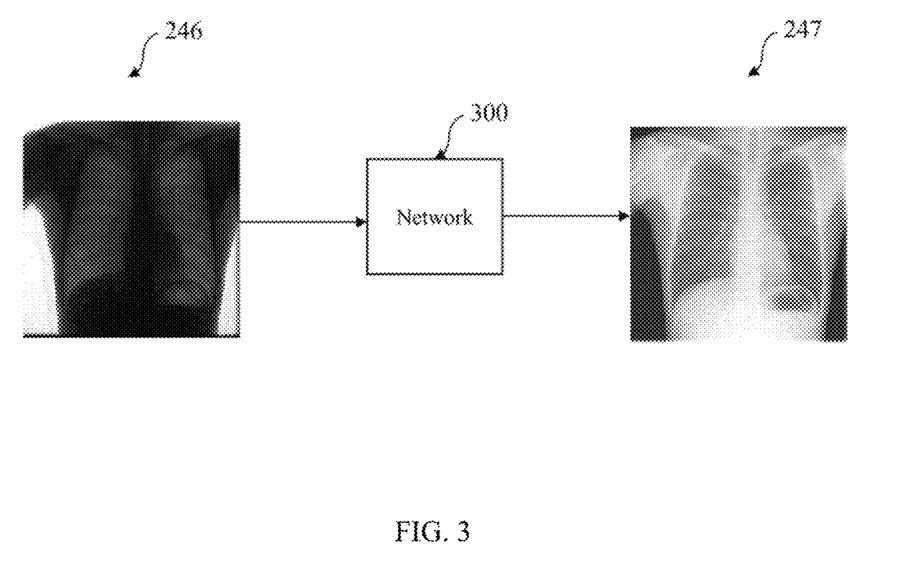
FIG. 3 is a schematic diagram of an optimization process according to some embodiments of the present invention.

FIG. 2 shows a medical imaging system 200 according to some embodiments of the present invention. FIG. 3 is a schematic diagram of an optimization process according to some embodiments of the present invention. As shown in FIGS. 2 to 3, the medical imaging system 200 includes a control module 210, a post-processing module 220, and a display module 230.

The control module 210 is configured to obtain an original image acquired by an X-ray imaging system.

In some embodiments, the detector 106 (as shown in FIG. 1) is used to acquire X-rays that pass through a detected object and are attenuated and perform data processing and reconstruction so as to obtain an original image, as shown by the original image 246 in FIG. 3, where the original image 246 may be displayed in the display module 230. In some embodiments, the control module 210 is connected to the control subsystem 108 (or computing device 120) disposed in the X-ray imaging system 100 shown in FIG. 1 or serves as part of the control subsystem 108 (or computing device 120).

The post-processing module 220 is configured to post-process the original image based on a trained network to obtain an optimized image after processing.

Specifically, as shown in FIG. 3, the original image 246 is inputted to the trained network 300, so that the optimized image 247 after post-processing can be obtained (outputted). In some embodiments, the optimized image 247 outputted by the post-processing module 220 may also be displayed in the display module 230. In some embodiments, the post-processing module 520 is connected to the control subsystem 108 (or computing device 120) disposed in the X-ray imaging system 100 shown in FIG. 1 or serves as part of the control subsystem 108 (or computing device 120).

In some embodiments, the medical imaging system 200 further includes a training module (not shown in the figure) for training the network 300 based on a sample original image set (known input) and a target image set (expected output). The network is completed through preparation of training data, selection and construction of a network model, and training, testing, and optimization of the network. In some embodiments, a training data set is stored in the storage device 122 of the X-ray imaging system 100, and the training module may train and/or update the network by obtaining the training data set.

In some embodiments, the training module is further configured to implement the following functions.

First, obtain a plurality of medical images acquired by the X-ray imaging system to serve as the sample original image set. In some embodiments, the sample original images are obtained after preprocessing is performed based on medical images reconstructed by the X-ray imaging system, where the preprocessing includes normalization or the like. In some other embodiments, unnormalized medical images may also be used as a sample image set and the sample image set is inputted to a network, and then the sample images are normalized based on a normalization layer in the network. In some other embodiments, the sample original images are obtained after being acquired and reconstructed by X-ray imaging systems of different models and normalized.

Second, obtain an optimized image after post-processing corresponding to each image in the sample original image set to serve as a target image set. In some embodiments, the post-processing includes one or a plurality of noise reduction, detail enhancement, and contrast adjustment processes. In some embodiments, the optimized image is obtained based on a conventional post-processing method, for example, obtained by manually adjusting one or a plurality of post-processing parameters and making judgment based on experience. However, those skilled in the art can understand that the obtaining of the optimized image is not limited to the aforementioned representation manner, and may also adopt any suitable manner.

Third: train a network by using the sample original image set as an input and the target image set as an output, so as to obtain the trained network.

In some other embodiments, the training module is further configured to implement the following functions.

First, obtain a plurality of medical images acquired by the X-ray imaging system to serve as the sample original image set.

Second, separately post-process each image in the sample original image set based on preferences of a plurality of users, so as to obtain a plurality of target image sets corresponding to preferences of each user. Some users prefer images with high contrast while some users prefer images with crisp details. In some embodiments, since users (such as doctors) have different preferences for optimized images, different post-processing may be performed on the sample original images according to preferences of the users so as to obtain a plurality of target image sets. For example, a first target image set corresponding to target images with high contrast, and a second target image set corresponding to target images with crisp details.

Third, train a network by using the sample original image set as an input and each of the plurality of target image sets as an output, so as to obtain one or a plurality of networks corresponding to the preferences of each user. For example, a first network is obtained by training using the sample original image set and the first target image set, the first network corresponds to users preferring high contrast, and an optimized image obtained by post-processing through the first network also has high contract; similarly, a second network is obtained by training using the sample original image set and the second target image set, the second network corresponds to users preferring crisp details, and an optimized image obtained by post-processing through the second network also has crisp details.

Figure 4:
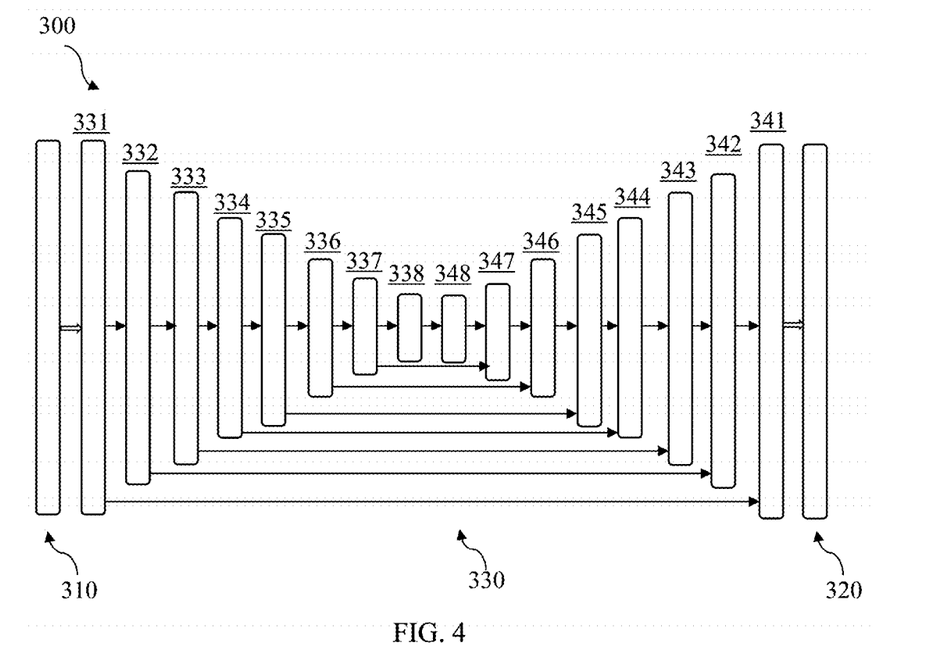
FIG. 4 is a schematic diagram of a network according to some embodiments of the present invention.

In some embodiments, the one or a plurality of networks are trained based on UNet or other well-known models. FIG. 4 is a schematic diagram of a network 300 according to some embodiments of the present invention. As shown in FIG. 4, the network 300 includes an input layer 310, processing layers (or referred to as hidden layers) 330, and an output layer 320.

In some embodiments, the processing layers 330 include an encoding part (331-338) and a decoding part (341-348). Specifically, the processing layers 330 include a first encoding layer 331 and a first decoding layer 341 in skip connection with the first encoding layer 331, a second encoding layer 332 and a second decoding layer 342 in skip connection therewith, a third encoding layer 333 and a third decoding layer 343 in skip connection therewith, a fourth encoding layer 334 and a fourth decoding layer 344 in skip connection therewith, a fifth encoding layer 335 and a fifth decoding layer 345 in skip connection therewith, a sixth encoding layer 336 and a sixth decoding layer 346 in skip connection therewith, a seventh encoding layer 337 and a seventh decoding layer 347 in skip connection therewith, and an eighth encoding layer 338 and an eighth decoding layer 348 in skip connection therewith, and the first to eighth encoding layers 331 to 338 and the first to eighth decoding layers 348 to 341 are also connected in sequence. The skip connection is set so that the output of a specific encoding layer can be directly transferred to a decoding layer in skip connection therewith rather than an adjacent layer (namely, a sequentially connected layer), and thus feature images of different levels (for example, different resolutions) can be outputted.

Although FIG. 4 shows that the processing layers include eight encoding layers and eight decoding layers, those skilled in the art should understand that the processing layers may include any number of encoding layers (the number of the decoding layers corresponds to the number of the encoding layers), which is not limited to eight, and the number of the encoding layers (or decoding layers) may be appropriately adjusted according to the number of pixels in sample images. In addition, those skilled in the art should understand that FIG. 4 only exemplarily shows the structure of the network and any other suitable configuration may be adopted.

In some embodiments, each layer of the first to eighth encoding layers 331 to 338 and the first to eighth decoding layers 341 to 348 includes at least one convolutional layer and at least one pooling layer, each convolutional layer and each pooling layer include several neurons, and the number of neurons in each layer may be the same or set differently according to needs. Based on sample original images (known input) and target images (expected output), the number of processing layers in a network and the number of neurons in each processing layer are set, and a weight and/or bias of the network is estimated (or adjusted or calibrated), so as to identify a mathematical relationship between the known input and the expected output and/or identify a mathematical relationship between the input and output of each layer.

Specifically, when the number of neurons in one of the layers is n, and corresponding values of the n neurons are $X_1, X_2, \ldots$ and $X_n$; the number of neurons in a next layer connected to the layer is m, and corresponding values of the m neurons are $Y_1, Y_2, \ldots$ and $Y_m$, the two adjacent layers may be represented as:

$$Y_j = f(\Sigma_{i=1}^n W_{ji} X_i + B_j)$$

where $X_i$ represents a value corresponding to an ith neuron of the previous layer, $Y_j$ represents a value corresponding to a jth neuron of the next layer, $W_{ji}$ represents a weight, and $B_j$ represents a bias. In some embodiments, the function $f$ is a rectified linear unit (ReLU).

Thus, the weight $W_{ij}$ and/or bias $B_j$ is adjusted so that the mathematical relationship between the input and output of each layer can be identified, and thus a loss function converges, so as to train the network.

When the network has been created or trained, once an original image to be post-processed is inputted to the network, an optimized image after post-processing can be obtained.

In one embodiment, although the configuration of the network 300 is guided by dimensions such as priori knowledge, input, and output of an estimation problem, optimal approximation of required output data is implemented depending on or exclusively according to input data. In various alternative implementations, clear meaning may be assigned to some data representations in the network 300 using some aspects and/or features of data, an imaging geometry, a reconstruction algorithm, or the like, which helps to accelerate training. This creates an opportunity to separately train (or pre-train) or define some layers in the network 300.

In some embodiments, the aforementioned sample image sets (including the sample original image set and the corresponding target image set thereof) may be updated so as to update or optimize the trained network based on the new sample image sets, where the target image set may be obtained based on a conventional post-processing method (namely, adjusting one or a plurality of post-processing parameters and making judgment based on experience), or may be obtained based on the medical imaging method according to some embodiments of the present invention (namely, through the aforementioned trained network).

In some other embodiments, the aforementioned trained network is obtained based on training by a training module on an external carrier (for example, an apparatus outside the medical imaging system). In some embodiments, the training module trains the network based on the sample original image set and the corresponding target image set thereof obtained after post-processing and based on UNet or other well-known models. In some embodiments, the training system may include a first module configured to store a training data set (including the sample original image set and the target image set), a second module configured to perform training and/or update based on a model, and a network configured to connect the first module and the second module. In some embodiments, the first module includes a first processing unit and a first storage unit, where the first storage unit is configured to store the training data set, and the first processing unit is configured to receive a relevant instruction (for example, obtaining a training data set) and send the training data set according to the instruction. In addition, the second module includes a second processing unit and a second storage unit, where the second storage unit is configured to store a training model, and the second processing unit is configured to receive a relevant instruction and perform training and/or update of the network. In some other embodiments, the training data set may further be stored in the second storage unit of the second module, and the training system may not include the first module. In some embodiments, the network may include various connection types, such as wired or wireless communication links, or fiber-optic cables.

Once data (for example, a trained network) is generated and/or configured, the data can be replicated and/or loaded into the X-ray imaging system 100, which may also be accomplished in a different manner. For example, models may be loaded via a directional connection or link between the X-ray imaging system 100 and the control subsystem 108. In this regard, communication between different elements may be accomplished using an available wired and/or wireless connection and/or based on any suitable communication (and/or network) standard or protocol. Alternatively or additionally, the data may be indirectly loaded into the X-ray imaging system 100. For example, the data may be stored in a suitable machine-readable medium (for example, a flash memory card), and then the medium is used to load the data into the X-ray imaging system 100 (for example, by a user or an authorized person of the system on site); or the data may be downloaded to an electronic apparatus (for example, a notebook computer) capable of local communication, and then the apparatus is used on site (for example, by the user or authorized person of the system) to upload the data to the X-ray imaging system 100 via a direct connection (for example, a USB connector).

As discussed herein, the deep learning technology (also referred to as deep machine learning, hierarchical learning, deep structured learning, or the like) employs an artificial neural network for learning. The deep learning method is characterized by using one or a plurality of network architectures to extract or simulate data of interest. The deep learning method may be implemented using one or a plurality of processing layers (for example, an input layer, an output layer, a convolutional layer, a normalization layer, or a sampling layer, where processing layers of different numbers and functions may exist according to different deep network models), where the configuration and number of the layers allow a deep network to process complex information extraction and modeling tasks. Specific parameters (or referred to as "weight" or "bias") of the network are usually estimated through a so-called learning process (or training process). The learned or trained parameters usually result in (or output) a network corresponding to layers of different levels, so that extraction or simulation of different aspects of initial data or the output of a previous layer usually may represent the hierarchical structure or concatenation of layers. During image processing or reconstruction, this output may be represented as different layers with respect to different feature levels in the data. Thus, processing may be performed layer by layer. That is, an earlier or higher-level layer may correspond to extraction of "simple" features from input data and then these simple features are combined into a layer exhibiting features of higher complexity. In practice, each layer (or more specifically, each "neuron" in each layer) may process input data as output data representation using one or a plurality of linear and/or non-linear transformations (so-called activation functions). The number of the plurality of "neurons" may be constant between the plurality of layers or may vary from layer to layer.

As discussed herein, as part of initial training of a deep learning process to solve a specific problem, a training data set includes a known input value (for example, a sample image or a pixel matrix of the image subjected to coordinate transformation) and an expected (target) output value (for example, an image or an identification and judgment result) finally outputted in the deep learning process. In this manner, a deep learning algorithm can process the training data set (in a supervised or guided manner or an unsupervised or unguided manner) until a mathematical relationship between a known input and an expected output is identified and/or a mathematical relationship between the input and output of each layer is identified and represented. In the learning process, (part of) input data is usually used, and a network output is created for the input data. Afterwards, the created network output is compared with the expected output of the data set, and then a difference between the created and expected outputs is used to iteratively update network parameters (weight and/or bias). A stochastic gradient descent (SGD) method may usually be used to update network parameters. However, those skilled in the art should understand that other methods known in the art may also be used to update network parameters. Similarly, a separate validation data set may be used to validate a trained network, where both a known input and an expected output are known. The known input is provided to the trained network so that a network output can be obtained, and then the network output is compared with the (known) expected output to validate prior training and/or prevent excessive training.

Figure 5:
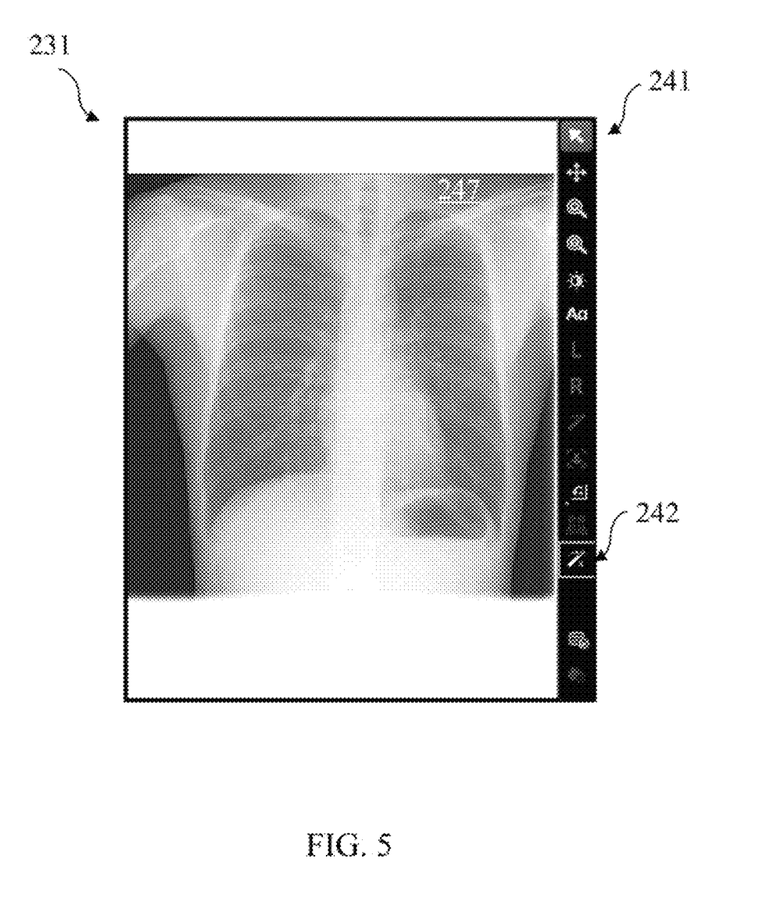
FIG. 5 is a schematic diagram of an image display interface of a display module in the medical imaging system shown according to FIG. 2.

Still referring to FIG. 2, the display module 230 is configured to display the original image and the optimized image. FIG. 5 shows an image display interface 231 of the display module 230 in the medical imaging system 200. As shown in FIG. 5, the image display interface 231 is configured to display the optimized image 247, and similarly, the original image 246 shown in FIG. 3 may also be displayed in the image display interface 231.

The display module 230 includes a first operating unit which is configured to generate a first instruction so as to input the original image 246 to the network 300. For example, the first operating unit is provided in the image display interface 231. Specifically, the first operating unit is provided in a menu bar 241 of the image display interface 231. More specifically, the first operating unit is a post-processing control option 242 in the menu bar 241. In some embodiments, a user may trigger the first operating unit to obtain the first instruction. Specifically, the user may select the option 242 through a mouse or an external input apparatus, or may select the option 242 by touch.

The display module 230 includes a second operating unit which is configured to generate a second instruction so as to select one network from the one or a plurality of networks to post-process the original image 246. In some embodiments, the second operating unit is provided in the menu bar 241 of the image display interface 231. More specifically, the first operating unit is a network selection option (not shown in the figure) in the menu bar 241. The user may trigger the first operating unit to obtain the first instruction. Specifically, the user may select the option through a mouse or an external input apparatus, or may select the option by touch. In some other embodiments, the second operating unit is provided in a user login interface. When the user logs in to his own account, the system can automatically identify or select a network corresponding to the user. Optionally, after the user logs in to his own account, a network selection interface pops up so that the user can manually select a required network (namely, corresponding to a desired optimized image style).

Although the aforementioned embodiment illustrates that the second operating unit is provided in the display module, those skilled in the art can understand that the second operating unit may also be provided in any other control apparatus or system. For example, a card reader provided in a control room may be used to identify an ID of a user, so as to automatically select a network corresponding to the user.

The display module 230 includes a third operating unit which is configured to generate a third instruction so as to input the original image and the optimized image to the network to optimize the network. For example, the third operating unit is provided in the menu bar 241 of the image display interface 231. Specifically, the third operating unit is a network optimization option (not shown in the figure) in the menu bar 241. In some embodiments, the user may trigger the third operating unit to obtain the third instruction. Specifically, the user may select the option through a mouse or an external input apparatus, or may select the option by touch.

In some embodiments, the menu bar 241 in the image display interface 231 may further include an operating unit such as zoom-in or zoom-out or movement.

Although FIG. 5 only shows that the menu bar 241 is located on the left side of the image display interface, those skilled in the art can understand that the menu bar 241 can be displayed in any manner and/or at any position and/or in any style. For example, a floating window may exist, all menu options can be expanded by selection, or the menu bar may be provided in a row on the lower side of the display interface. In addition, although the image display interface 231 in FIG. 5 only shows the optimized image 247 and the menu bar 241, those skilled in the art should understand that the image display interface 231 may further display other types of content. For example, the display portion of the optimized image may further include, on the left side, other content such as the address of the image, or switching control of a plurality of images (the original image and the optimized image). In some embodiments, the original image and the optimized image may also be displayed in the same graphical user interface.

In some embodiments, the display module 230 is the display device 124 (as shown in FIG. 1) in the X-ray imaging system, and the display module 230 includes a control display disposed in a scanning room (or an equipment room) and/or a display disposed in the control room.

Figure 6:
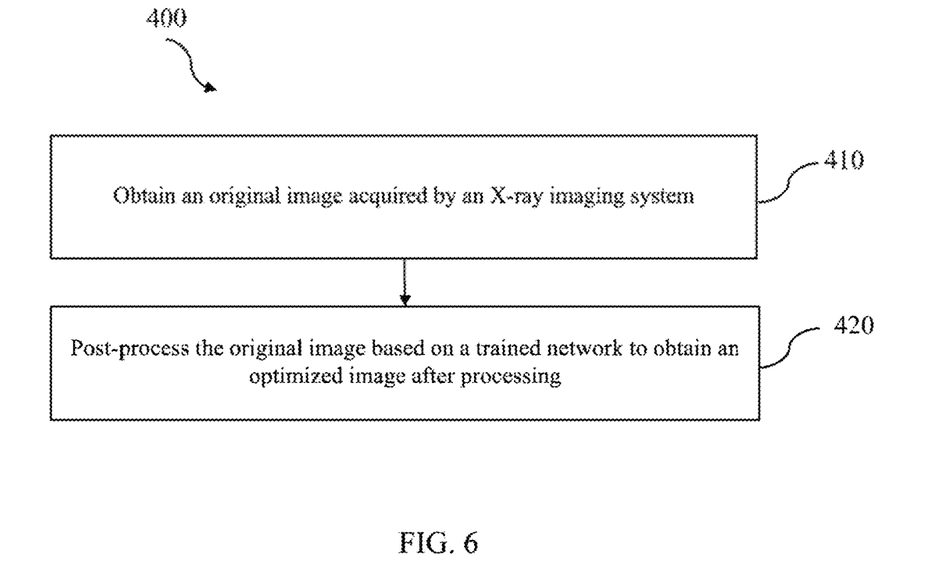
FIG. 6 is a flowchart of a medical imaging method according to some embodiments of the present invention.

FIG. 6 is a flowchart of a medical imaging method 400 according to some embodiments of the present invention. As shown in FIG. 6, the medical imaging method 400 in some embodiments of the present invention includes steps 410 and 420.

Step 410: obtain an original image acquired by an X-ray imaging system.

In some embodiments, a detector is used to acquire X-rays that pass through a detected object and are attenuated and perform data processing and reconstruction so as to obtain a medical image, where the original image may be displayed in a display device or display module in the X-ray imaging system.

Step 420: post-process the original image based on a trained network to obtain an optimized image after processing. Specifically, the original image is inputted to the trained network, so that the optimized image after post-processing can be obtained (outputted), where the optimized image can also be displayed in the display apparatus of the X-ray imaging system.

In some embodiments, the network is completed through preparation of training data, selection and construction of a network model, and training, testing, and optimization of the network. In some embodiments, the one or a plurality of networks are trained based on UNet or other well-known models, where the network is trained based on a sample original image set and a target image set. Specifically, the training of the network includes the following step 1 to step 3.

Step 1: obtain a plurality of medical images acquired by the X-ray imaging system to serve as the sample original image set. In some embodiments, the sample original images are obtained after preprocessing is performed based on medical images reconstructed by the X-ray imaging system, where the preprocessing includes normalization or the like. In some embodiments, the sample original images are obtained after being acquired and reconstructed by X-ray imaging systems of different models and normalized.

Step 2: obtain an optimized image after post-processing corresponding to each image in the sample original image set to serve as a target image set. In some embodiments, the post-processing includes one or a plurality of noise reduction, detail enhancement, and contrast adjustment processes. In some embodiments, the optimized image is obtained based on a conventional post-processing method, for example, obtained by manually adjusting one or a plurality of post-processing parameters and making judgment based on experience. However, those skilled in the art can understand that the obtaining of the optimized image is not limited to the aforementioned representation manner, and may also adopt any suitable manner.

Step 3: train a network by using the sample original image set as an input and the target image set as an output, so as to obtain the trained network.

In some other embodiments, the training of the network includes the following step 1 to step 3.

Step 1: obtain a plurality of medical images acquired by the X-ray imaging system to serve as the sample original image set.

Step 2: separately post-process each image in the sample original image set based on preferences of a plurality of users, so as to obtain a plurality of target image sets corresponding to preferences of each user. Some users prefer images with high contrast while some users prefer images with crisp details. In some embodiments, since users (such as doctors) have different preferences for optimized images, different post-processing may be performed on the sample original images according to preferences of the users so as to obtain a plurality of target image sets. For example, a first target image set corresponding to target images with high contrast, and a second target image set corresponding to target images with crisp details.

Step 3: train a network by using the sample original image set as an input and each of the plurality of target image sets as an output, so as to obtain one or a plurality of networks corresponding to the preferences of each user. For example, a first network is obtained by training using the sample original image set and the first target image set, the first network corresponds to users preferring high contrast, and an optimized image obtained by post-processing through the first network also has high contract; similarly, a second network is obtained by training using the sample original image set and the second target image set, the second network corresponds to users preferring crisp details, and an optimized image obtained by post-processing through the second network also has crisp details.

In some embodiments, before step 420 (post-processing the original image based on a trained network to obtain an optimized image after processing), the method further includes inputting the original image to the network based on a first instruction of a user. Specifically, the first instruction is triggered based on a first operating unit in an image display interface.

In some embodiments, the trained network includes one or a plurality of networks. The medical imaging method 400 further includes selecting one from the one or a plurality of networks based on a second instruction of the user, so as to post-process the original image. In some embodiments, the second instruction of the user is triggered based on identification of the user. In some other embodiments, the second instruction of the user is triggered based on a second operating unit in the image display interface.

In some embodiments, the medical imaging method 400 further includes further inputting the original image and the optimized image to the network based on a third instruction of the user, so as to optimize the network. Specifically, the third instruction is triggered based on a third operating unit in the image display interface.

The medical imaging method based on deep learning proposed in the present invention can post-process a medical original image in a more accurate and timely manner. As manual adjustment by an on-site engineer or experience-based judgment would no longer be required, the difficulty of parameter adjustment would be lowered and the adjustment time in the post-processing process would be reduced. The image quality of an optimized image obtained after post-processing would also be improved. In addition, sample image sets of different styles can also be set according to preferences (or styles) of users, so as to train learning networks of different styles. Corresponding learning networks are also selected by users, so that optimized image styles corresponding to the user preferences can be obtained.

The present invention may further provide a non-transitory computer-readable storage medium for storing an instruction set and/or a computer program. When executed by a computer, the instruction set and/or computer program causes the computer to perform the aforementioned medical imaging method. The computer executing the instruction set and/or computer program may be a computer of an X-ray imaging system, or may be other devices/modules of the X-ray imaging system. In one embodiment, the instruction set and/or computer program may be programmed into a processor/controller of the computer.

Specifically, when executed by the computer, the instruction set and/or computer program causes the computer to:
 obtain an original image acquired by an X-ray imaging system; and
 post-processing the original image based on a trained network to obtain an optimized image after processing.

The instructions described above may be combined into one instruction for execution, and any of the instructions may also be split into a plurality of instructions for execution. Moreover, the present invention is not limited to the instruction execution order described above.

In some embodiments, before post-processing the original image, the method further includes inputting the original image to the network based on a first instruction of a user.

In some embodiments, the trained network includes one or a plurality of networks, and the method further includes selecting one from the one or a plurality of networks based on a second instruction of the user, so as to post-process the original image.

In some embodiments, the method further includes further inputting the original image and the optimized image to the network based on a third instruction of the user, so as to optimize the network.

As used herein, the term "computer" may include any processor-based or microprocessor-based system including a system that uses a microcontroller, a reduced instruction set computer (RISC), an application specific integrated circuit (ASIC), a logic circuit, and any other circuit or processor capable of executing the functions described herein. The above examples are merely exemplary and thus are not intended to limit the definition and/or meaning of the term "computer" in any way.

The instruction set may include various commands that instruct a computer acting as a processor or instruct a processor to perform particular operations, such as the methods and processes of various embodiments. The instruction set may be in the form of a software program, and the software program can form part of one or a plurality of tangible, non-transitory computer-readable media. The software may be in various forms such as system software or application software. In addition, the software may be in the form of a set of independent programs or modules, a program module within a larger program, or part of a program module. The software may also include modular programming in the form of object-oriented programming. The input data may be processed by the processor in response to an operator command, or in response to a previous processing result, or in response to a request made by another processor.

Some exemplary embodiments have been described above; however, it should be understood that various modifications may be made. For example, if the described techniques are performed in a different order and/or if the components of the described system, architecture, apparatus, or circuit are combined in other manners and/or replaced or supplemented with additional components or equivalents thereof, a suitable result can be achieved. Accordingly, other implementation manners also fall within the protection scope of the claims.

The invention claimed is:

1. A medical imaging method, comprising:
obtaining an original image acquired by an X-ray imaging system; and
post-processing the original image based on a trained network to obtain an optimized image after processing;
wherein the network is trained based on a sample original image set and a target image set; and
wherein the training method comprises:
   obtaining a plurality of original images acquired by the X-ray imaging system, so as to obtain the sample original image set;
   separately post-processing the original images based on preferences of one or a plurality of users, so as to obtain a plurality of target image sets corresponding to preferences of each user; and
   training a neural network by using the sample original image set as an input and each of the plurality of target image sets as an output, so as to obtain one or a plurality of networks corresponding to the preferences of each user.

2. The method according to claim 1, wherein before post-processing the original image, the method further comprises inputting the original image to the network based on a first instruction of a user.

3. The method according to claim 2, wherein the first instruction is triggered based on a first operating unit in an image display interface.

4. The method according to claim 1, wherein the trained network comprises one or a plurality of networks, and the method further comprises:
selecting one from the one or a plurality of networks based on a second instruction of the user, so as to post-process the original image.

5. The method according to claim 4, wherein the second instruction of the user is triggered based on identification of the user.

6. The method according to claim 4, wherein the second instruction of the user is triggered based on a second operating unit in the image display interface.

7. The method according to claim 1, further comprising:
further inputting the original image and the optimized image to the network based on a third instruction of the user, so as to optimize the network.

8. The method according to claim 7, wherein the third instruction is triggered based on a third operating unit in the image display interface.

9. A non-transitory computer-readable storage medium for storing a computer program, wherein when executed by a computer, the computer program causes the computer to perform the medical imaging method according claim 1.

10. A medical imaging system, comprising:
a control module, configured to obtain an original image acquired by an X-ray imaging system;
a post-processing module, configured to post-process the original image based on a trained network to obtain an optimized image after processing;
a display module, configured to display the original image and the optimized image; and
a training module, configured to train the network based on a sample original image set and a target image set;
wherein the training module is further configured to:
   obtain a plurality of original images acquired by the X-ray imaging system, so as to obtain the sample original image set;
   separately post-process the original images based on preferences of one or a plurality of users, so as to obtain a plurality of target image sets corresponding to preferences of each user; and
   train a neural network by using the sample original image set as an input and each of the plurality of target image sets as an output, so as to obtain one or a plurality of networks corresponding to the preferences of each user.

11. The system according to claim 10, wherein the display module comprises a first operating unit configured to generate a first instruction so as to input the original image to the network.

* * * * *